United States Patent [19]

Nakazawa et al.

[11] Patent Number: 4,942,172

[45] Date of Patent: Jul. 17, 1990

[54] METHOD OF CURING HEPATIC DISEASE

[75] Inventors: Hitoshi Nakazawa, Narita; Mari Ohtsuka, Narashino; Hideaki Matsuda, Abiko; Tatsuhiko Katori, Tone; Kazuhiko Irinoda, Chiba, all of Japan

[73] Assignee: SS Pharmaceutical Co., Ltd., Tokyo, Japan

[21] Appl. No.: 196,431

[22] Filed: May 20, 1988

[30] Foreign Application Priority Data

Sep. 25, 1987 [JP] Japan .................................. 62-241543
Jan. 21, 1988 [JP] Japan .................................. 63-11075

[51] Int. Cl.$^5$ ............................................ A61K 31/385
[52] U.S. Cl. ...................................... 514/441; 514/894
[58] Field of Search ............... 514/441, 893, 894, 838; 549/36

[56] References Cited

U.S. PATENT DOCUMENTS

| 4,034,102 | 7/1977 | Taninaka | 514/441 |
| 4,080,466 | 3/1978 | Taninaka et al. | 514/441 |
| 4,080,467 | 3/1978 | Taninaka et al. | 514/441 |

FOREIGN PATENT DOCUMENTS

| 16820 | 7/1982 | Japan | 514/893 |
| 9204187 | 4/1983 | Japan | 514/441 |
| 6682 | 6/1983 | Japan | 514/441 |
| 6691 | 6/1983 | Japan | 514/441 |
| 199892 | 3/1984 | Japan | 514/441 |
| 16819 | 7/1987 | Japan | 514/893 |

OTHER PUBLICATIONS

Culvenor, "Reactions of Ethylene Oxide", J. Chem. Soc., pp. 1050–1052, (1946).
Chen, "Easy Synthesis of 1,3 Dithiole-2-Thione", J. Chem. Soc., Chemical Communications, pp. 920–921, (1976).

Primary Examiner—Douglas W. Robinson
Assistant Examiner—Roger Gobrogge
Attorney, Agent, or Firm—Oblon, Spivak, McClelland, Maier & Neustadt

[57] ABSTRACT

A method of curing or alleviating hepatic disease comprising administrating to the patient 1,3-dithiole-2-thione or 1,3-dithiolane-2-thione is disclosed. Administration of the compound can be made in various dosing forms, including tablets, granules, powders, capsules, suspensions, injections, and suppositories. Normal dosing amount can be determined from the range of 0.01 to 50 mg/kg/day for oral administration, and 0.002 to 10 mg/kg/day for injection or other forms of administration.

7 Claims, No Drawings

METHOD OF CURING HEPATIC DISEASE

BACKGROUND OF THE INVENTION

1. Field of the Invention

This invention relates to a method of curing or alleviating hepatic diseases.

2. Description of the Background

Very few therapeutic agents have been known in the art which are effective for serious hepatic diseases such as cirrhosis of the liver or the like. Only diisopropyl-1,3-dithiol-2-ylidenemalonate (generally known as Malotilate), which has an amelioration effect of liver protein metabolism, is known as a medicine effective against cirrhosis of the liver.

However, since Malotilate is known to have side effects, there has been a need for the development of a compound which is safer than Malotilate and has the same or better pharmaceutical effect. Various kinds of 1,3-dithioles and 1,3-dithiolane derivatives have been synthesized with the intention of providing such a compound. However, none of them are yet satisfactory in terms of their pharmaceutical effect and safety. Therefore, there still exists a strong need for a compound which gives both the pharmaceutical effect and is safe.

In view of this situation, the present inventors have conducted extensive screenings on a number of compounds with respect to their therapeutic effect on hepatic diseases and their safety, and as a result have found that certain cyclic sulfur-containing compounds are excellent therapeutic agents for hepatic diseases and can satisfy the requirements of therapeutic effectiveness and safety. Such a finding has led to the completion of this inention.

SUMMARY OF THE INVENTION

Accordingly an object of this invention is to provide a a method of curing or alleviating hepatic diseases such as cirrhosis, alcoholic hepatitis, virus-derived hepatitis, and the like, which comprises administrating to a patient an effective amount of a cyclic sulfur-containing compound represented by the following formula (I):

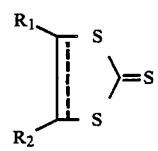

in which the dotted line is optionally present. The groups $R_1$ and $R_2$ may independently be selected from hydrogen; $C_{1-20}$ alkyl groups (e.g., methyl, ethyl, isobutyl, dodecyl) which are optionally substituted with halogen (i.e. F, Br, Cl, I), hydroxyl, lower alkoxy, amino, lower alkylamino, carboxyl, lower alkoxycarbonyl, cyano, $C_{6-10}$ aryl (e.g. phenyl, naphthyl) or the like; $C_{2-12}$ alkenyl groups (e.g. vinyl, allyl, isobutenyl, decenyl) which may optionally be substituted with halogen (i.e. F, Br, Cl, I), hydroxyl, carboxyl, $C_{6-10}$ aryl (e.g. phenyl, naphthyl) or the like; $C_{6-10}$ aryl (e.g. phenyl, naphthyl) groups which may optionally be substituted with halogen (i.e. F, Br, Cl, I), lower alkyl, hydroxyl, lower alkoxy, amino, lower alkylamino, carboxyl, lower alkoxycarbonyl, cyano, nitro, $C_{6-10}$ aryl (e.g. phenyl, naphthyl), $C_{6-10}$ aryloxy (e.g. phenoxy, naphthoxy), sulfonyl, formyl, carbamoyl, $C_{1-6}$ acyl (e.g. acetyl), $C_{7-11}$ aroyl (e.g. benzoyl, naphthoyl), or the like. By lower is meant $C_{1-4}$ groups.

In a preferred embodiment of the invention, $R_1$ and $R_2$ are independently selected from hydrogen, $C_{1-4}$ alkyl groups, $C_{2-4}$ alkenyl groups, and $C_{6-7}$ aryl groups.

In a more preferred embodiment, $R_1$ and $R_2$ are each hydrogen.

Other objects, features and advantages of the invention will hereinafter become more readily apparent from the following description.

DETAILED DESCRIPTION OF THE INVENTION AND PREFERRED EMBODIMENTS

The compounds shown by the above formula (I), wherein $R_1$ and $R_2$ are H, are known compounds. The compound with the dotted line, i.e., the compound of the following chemical structure (Ia) is 1,3-dithiole-2-thione. This compound was synthesized by R. Mayer et al [*Chemische Berichte*, 97, 1298 (1964)] and C. H. Chen [*J. Chem. Soc., Chemical Communication*, 920–921 (1976)].

The compound without the dotted line in formula (I), which has the chemical structure (Ib), is 1,3-dithiolane-2-thione, and was synthesized by C. C. J. Culvenor et al [*J. Chem. Soc.* 1050–1052 (1946)]

The substituted derivatives of (I) may be prepared from appropriately substituted starting materials.

However, to the inventors' knowledge there have been no reports in the art on any pharmaceutical effects of these compounds.

Hereinafter are presented experimental examples to further illustrate the effectiveness of the invention. These examples are given for illustration of the invention and are not intended to be limiting thereof.

EXPERIMENTAL EXAMPLES

As shown in the test described below, in which hepatic disorder was experimentally induced in animals by the administration of carbon tetrachloride or galactosamine, the compound (Ia) depressed changes in the outward appearance of the liver, and (Ia) and (Ib) exhibited a remarkable suppression of GOT and GPT activities in serum. While the following experimental examples were carried out with (Ia) and (Ib), the substituted derivatives of (I) are expected to show similar therapeutic results.

EXPERIMENTAL EXAMPLE 1

Several groups of ddY male mice, each group consisting of 5 mice, aged 5 weeks and weighing approximately 25 g, were provided for the test. The mice were fasted for 16 hours and were given 0.05 ml/kg of carbon tetrachloride mixed with olive oil by oral administration to provide a dose (as a mixture of carbon tetrachloride and olive oil) of 10 ml/kg. At the same time, 1,3-dithiole-2-thione (Ia), 1,3-dithiolane-2-thione (Ib), or Malotilate, the comparative agent, each dissolved in olive oil to give the prescribed concentration, was given to each mouse in a given group. Blood was collected from each mouse at 24 hours after administration for measurement of GOT and GPT activities in serum. The results are shown in Table 1 below.

TABLE 1

|  | Dose (mg/kg p.o.) | GOT (IU/L) | GPT (IU/L) |
|---|---|---|---|
| Control Group | — | 80 | 30 |
| Groups given only carbon tetrachloride | — | 12700 | 6340 |
| Groups given carbon tetrachloride and compound (Ia) | 0.1 | 5740 | 3880 |
|  | 1 | 110 | 30 |
|  | 10 | 90 | 30 |
| Groups given carbon tetrachloride | 8 | 130 | 40 |
|  | 40 | 90 | 20 |
| and compound (Ib) | 200 | 70 | 20 |
| Groups given carbon tetrachloride and Malotilate | 20 | 8540 | 6260 |
|  | 100 | 3220 | 2290 |
|  | 500 | 440 | 310 |

Histological observations were made on the test animals to detect the presence of a liver necrosis. As a result, a centrilobular liver necrosis was found in animals of the group to which only carbon tetrachloride had been administered, while in the groups to which 100 mg/kg or more of Malotilate were given, the degree of centrilobular liver necrosis was less significant than in the group of animals to which only carbon tetrachloride had been administered. On the other hand, there was no centrilobular liver necrosis observed in animals of the groups to which 1 mg/kg or more of the compound (Ia) was administered.

EXPERIMENTAL EXAMPLE 2

Several groups of Wister male rats, each group consisting of 4 rats, age 6 weeks, were provided for the test. The rats were not fed overnight, and 1 ml/kg of carbon tetrachloride as a 20% solution in olive oil was subcutaneously injected into each rat. At the same time, a prescribed amount of 1,3-dithiole-2-thione (Ia) or Malotilate was administered orally to each rat. Blood was collected from each rat at 48 hours after administration for measurement of GOT, GPT, ALP, and LDH activities as well as TCHO and GLU concentrations in serum. The results are shown in Table 2.

TABLE 2

|  | Dose (mg/kg p.o.) | GOT (IU/L) | GPT (IU/L) | ALP (IU/L) | LDH (IU/L) | TCHO (mg/dl) | GLU (mg/dl) |
|---|---|---|---|---|---|---|---|
| Control Group | — | 110 | 30 | 1525 | 2968 | 81 | 13 |
| Groups given only carbon tetrachloride | — | 6170 | 2080 | 3322 | 2203 | 109 | 10 |
| Groups given carbon tetrachloride and compound (Ia) | 0.08 | 5910 | 2020 | 2775 | 2707 | 105 | 11 |
|  | 0.4 | 3420 | 1160 | 2622 | 2792 | 75 | 11 |
|  | 2 | 750 | 280 | 2075 | 3022 | 63 | 13 |
|  | 10 | 900 | 360 | 2262 | 2393 | 55 | 12 |
| Groups given carbon tetrachloride and Malotilate | 4 | 9040 | 2610 | 2989 | 4010 | 112 | 10 |
|  | 20 | 4390 | 1550 | 2513 | 3195 | 117 | 11 |
|  | 100 | 3450 | 1180 | 2325 | 4204 | 129 | 11 |
|  | 500 | 900 | 300 | 1687 | 3765 | 101 | 13 |

EXPERIMENTAL EXAMPLE 3

Several groups of Wister male rats, each group consisting of 5 rats, age 5 weeks, were provided for the test. To each of the rats 1,3-dithiole-2-thione (Ia) or Malotilate, each dissolved in olive oil, was administered orally. Six (6) hours later 400 mg/kg of D-galactosamine was abdominally administered. Blood was collected from each rat at 24 hours after administration of D-galactosamine for measurement of GOT, GPT, ALP, and LDH activities as well as TCHO and GLU concentrations in serum. The results are shown in Table 3.

TABLE 3

|  | Dose (mg/kg p.o.) | GOT (IU/L) | GPT (IU/L) | ALP (IU/L) | LDH (IU/L) | TCHO (mg/dl) | GLU (mg/dl) |
|---|---|---|---|---|---|---|---|
| Control Group | — | 96 | 28 | 1370 | 2140 | 77 | 14 |
| Groups given only D-galactosamine | — | 616 | 288 | 2117 | 3468 | 43 | 11 |
| Groups given D-galactosamine and compound (Ia) | 2 | 360 | 156 | 1815 | 2984 | 35 | 10 |
|  | 10 | 380 | 148 | 1900 | 2708 | 33 | 12 |
|  | 50 | 196 | 72 | 1791 | 2220 | 66 | 14 |
| Groups given D-galactosamine and Malotilate | 20 | 596 | 256 | 1977 | 3504 | 30 | 10 |
|  | 100 | 268 | 96 | 1990 | 2604 | 41 | 12 |
|  | 500 | 248 | 76 | 1900 | 3492 | 56 | 12 |

As is evident from the above results, the administration of carbon tetrachloride or D-galactosamine brings about a significant increase in values of GOT, GPT and ALP in serum of as much as 1.5 times or much more. Also, it is shown that administration of the compounds (Ia) or (Ib), or Malotilate decreases these values almost dose dependently. Such meaningful decrease can be realized with respect to compound (Ia) at a dose of about 2 mg/kg, and with respect to Malotilate at a dose of at least 100 mg/kg or more. The $LD_{50}$ value of the compound (Ia) is from 125 to 250 mg/kg (mouse; p.o.) and that of the compound (Ib) is not less than 500 mg/kg (mouse; p.o.). This evidence suggests that the compounds of formula (Ia) and (Ib) are safer than Malotilate. More specifically, from the $ED_{50}$ values determined from the results shown in Table 2, the safety coefficient ($LD_{50}/ED_{50}$) for compound (Ia) can be calculated as 260.4–520.8. On the other hand, Malotilate, which has an $LD_{50}$ value of 4,000–8,000 mg/kg and an $ED_{50}$ value of 118 mg/kg as determined from Table 2, has a safety coefficient ($LD_{50}/ED_{50}$) of 33.9–67.8.

Thus, it is concluded that the compound (Ia) of the present invention is 4–15 times safer than Malotilate.

As illustrated above, the compounds (Ia) and (Ib) exhibit a remarkably high liver disorder suppressing effect and safety as compared with the comparative agent Malotilate. It is expected that similar results would be obtained with the substituted derivatives of (I).

Although the amount of dosage of the compound (I) used as a hepatic disease therapeutic agent may vary depending on the body weight, age, sex of the subject, the manner by which it is administered, the conditions and significance of disease of the subject, and the like, a generally appropriate amount may be from 0.01 to 50 mg per day per kg of body weight of the subject when it is orally administered, and from 0.002 to 10 mg per day per kg of body weight when it is otherwise administered.

The hepatic disease therapeutic agent used in the method of the present invention can be prepared in various dosing forms according to conventional methods, such as tablets, granules, powders, capsules, suspensions, injections, suppositories, or the like. When it is prepared in a solid dosing form for oral administration, various additives such as a binder, disintegrator, glossing agent, coloring agent, flavor, extending agent, coating agent, sugar coating agent, and the like, are compounded as appropriate, and then formed into tablets, granules, powders, capsules, or the like according to conventional methods. When an injection is prepared using this compound (I) as a main active agent, the compound is dissolved as required in an oil or fat such as olive oil, sesame oil, or the like, and made into a liquid for subcutaneous muscle injection. Alternatively, it is possible to prepare an intravenous injection liquid or an infusion fluid by adding a surface active agent to the formulation. A suppository ca be prepared by adding coconut butter or a medium-chain fat fatty acid glycerol ester to the compound (I), and by heating and kneading the mixture before shaping it into a suppository.

Other features of the invention will become apparent in the course of the following description of the exemplary embodiments which are given for illustration of the invention and are not intended to be limiting thereof.

FORMULATION EXAMPLES

| Example 1 Tablet | |
|---|---|
| 1,3-dithiole-2-thione (Ia) | 50 mg |
| crystallized cellulose | 50 mg |
| lactose | 50 mg |
| hydroxypropylcellulose | 18 mg |
| magnesium stearate | 2 mg |
| Total | 170 mg |

The tablet of the above composition ca be made into a sugar coated or film coated tablet.

| Example 2 Capsule | |
|---|---|
| 1,3-dithiole-2-thione (Ia) | 50 mg |
| light silicic acid anhydride | 25 mg |
| lactose | 100 mg |
| starch | 50 mg |
| talc | 25 mg |
| Total | 250 mg |

The above components were filled in a No. 1 capsule.

| Example 3 Granule | |
|---|---|
| 1,3-dithiole-2-thione (Ia) | 50 mg |
| lactose | 600 mg |
| corn starch | 200 mg |
| sodium carboxymethylcellulose | 20 mg |
| hydroxypropylcellulose | 130 mg |
| Total | 1,000 mg |

The above amounts of the components were made into a granule by a conventional method.

| Example 4 Powder | |
|---|---|
| 1,3-dithiole-2-thione (Ia) | 50 mg |
| light silicic acid anhydride | 20 mg |
| precipitating calcium carbonate | 10 mg |
| lactose | 250 mg |
| starch | 70 mg |
| Total | 400 mg |

The above amounts of the components were made into a powder by a conventional method.

| Example 5 Suppository | |
|---|---|
| 1,3-dithiole-2-thione (Ia) | 10 mg |
| coconut butter | 890 mg |
| Total | 900 mg |

The above amounts of the components were made into a suppository by a conventional method.

| Example 6 Injection | |
|---|---|
| 1,3-dithiole-2-thione (Ia) | 10 mg |
| hydrogenated castor oil | 80 mg |
| propylene glycol | 60 mg |
| dextrose | 50 mg |

The above components were dissolved in distilled water for injection to make the total volume to 1 ml to prepare an injection fluid by a conventional method.

| Example 7 Tablet | |
|---|---|
| 1,3-dithiole-2-thione (Ia) | 2 mg |
| crystallized cellulose | 74 mg |
| lactose | 74 mg |
| hydroxypropylcellulose | 18 mg |
| magnesium stearate | 2 mg |
| Total | 170 mg |

The tablet of the above composition can be made into a sugar coated or film coated tablet.

| Example 8 Injection | |
|---|---|
| 1,3-dithiole-2-thione (Ia) | 1 mg |
| polyoxyethylene hydrogenated castor oil | 40 mg |
| propylene glycol | 60 mg |

The above components were dissolved in distilled water for injection to make the total volume to 1 ml to prepare an injection fluid by a conventional method.

| Example 9 Tablet | |
|---|---|
| 1,3-dithiolane-2-thione (Ib) | 50 mg |
| crystallized cellulose | 50 mg |
| lactose | 50 mg |
| hydroxypropylcellulose | 18 mg |
| magnesium stearate | 2 mg |
| Total | 170 mg |

The tablet of the above composition can be made into a sugar coated or film coated tablet.

| Example 10 Injection | |
|---|---|
| 1,3-dithiolane-2-thione (Ib) | 10 mg |
| polyoxyethylene hydrogenated castor oil | 40 mg |
| propylene glycol | 60 mg |

The above components were dissolved in distilled water for injection to make the total volume to 1 ml to prepare an injection fluid by a conventional method.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States of America is:

1. A method of curing of alleviating hepatic disease in a mammal suffering from a hepatic disease selected from the group consisting of cirrhosis, alcoholic hepatitis, and virus-derived hepatitis, comprising: administrating to said mammal a therapeutically effective amount of a cyclic sulfur-containing compound represented by the following formula (I):

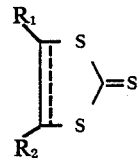

wherein the dotted line is optionally present and wherein the groups $R_1$ and $R_2$ are independently selected from the group consisting of hydrogen; $C_{1-20}$ alkyl groups and $C_{2-12}$ alkenyl groups.

2. The method according to claim 1, wherein $R_1$ and $R_2$ are independently selected from the group consisting of hydrogen, $C_{1-4}$ alkoxy groups, and $C_{2-4}$ alkenyl groups.

3. A method according to claim 1, wherein $R_1$ and $R_2$ are each hydrogen.

4. A method according to claim 1, wherein said compound is administered in combination with a pharmacologically acceptable carrier.

5. A method according to claim 1, wherein the mammal is a human being.

6. A method according to claim 1, wherein the compound (I) is administered orally in an amount of from 0.01 to 50 mg per day per kg of body weight of said mammal.

7. A method according to claim 1, wherein the compound (I) is administered by intramuscular injection, intravenous injection, infusion fluid, or suppository in an amount of from 0.002 to 10 mg per day per kg of body weight of said mammal.

* * * * *

UNITED STATES PATENT AND TRADEMARK OFFICE
CERTIFICATE OF CORRECTION

PATENT NO. : 4,942,172

DATED : July 17, 1990

INVENTOR(S) : HITOSHI NAKAZAWA ET AL

It is certified that error appears in the above-identified patent and that said Letters Patent is hereby corrected as shown below:

| Col. | Line |
|---|---|
| 8 | 24, delete "alkoxy" and insert --alkyl--. |

Signed and Sealed this

Nineteenth Day of May, 1992

Attest:

DOUGLAS B. COMER

*Attesting Officer*     Acting Commissioner of Patents and Trademarks